United States Patent [19]

Cragg

[11] Patent Number: 5,085,635
[45] Date of Patent: Feb. 4, 1992

[54] VALVED-TIP ANGIOGRAPHIC CATHETER

[76] Inventor: Andrew H. Cragg, 26 Oak Park Dr., Iowa City, Iowa 52240

[21] Appl. No.: 524,851

[22] Filed: May 18, 1990

[51] Int. Cl.$^5$ ............................................. A61M 29/00
[52] U.S. Cl. ...................................... 604/96; 604/102; 604/167; 604/256
[58] Field of Search ............... 604/9, 961, 102, 167, 604/169, 247, 256, 264, 280; 128/658

[56] References Cited

U.S. PATENT DOCUMENTS

| | | | |
|---|---|---|---|
| 3,726,283 | 4/1973 | Dye et al. | 604/247 |
| 4,023,559 | 5/1977 | Gaskell | 604/280 |
| 4,037,604 | 7/1977 | Newkirk | 604/247 |
| 4,475,902 | 10/1984 | Schubert | 604/256 |
| 4,850,969 | 7/1989 | Jackson | 604/96 |
| 4,871,356 | 10/1989 | Haindl et al. | 604/247 |

FOREIGN PATENT DOCUMENTS

| | | | |
|---|---|---|---|
| 8901352 | 2/1989 | PCT Int'l Appl. | 604/280 |
| 2069339 | 8/1981 | United Kingdom | 604/9 |

*Primary Examiner*—John D. Yasko
*Assistant Examiner*—Anthony Gutowski
*Attorney, Agent, or Firm*—James C. Nemmers

[57] ABSTRACT

An angiographic catheter is described with a valve covering the end-hole on the distal end. The valve will allow the catheter to be passed over a guidewire but will prevent an injected fluid (e.g., a contrast medium) from being discharged from the end hole. The valved-end catheter has side-holes near the distal end that provide for lateral discharge of the fluid thereby preventing the creation of an end-hole jet and the resulting undesirable effects of the jet.

6 Claims, 1 Drawing Sheet

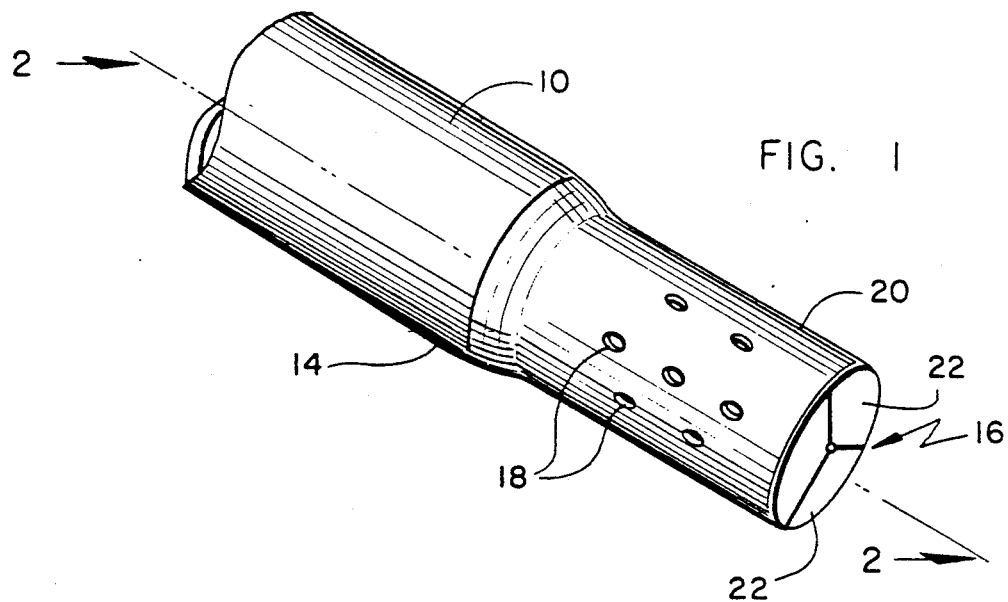
FIG. 1
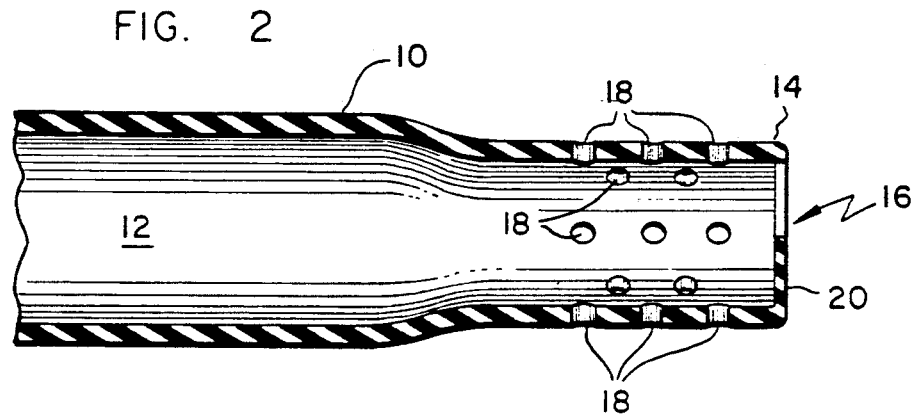
FIG. 2
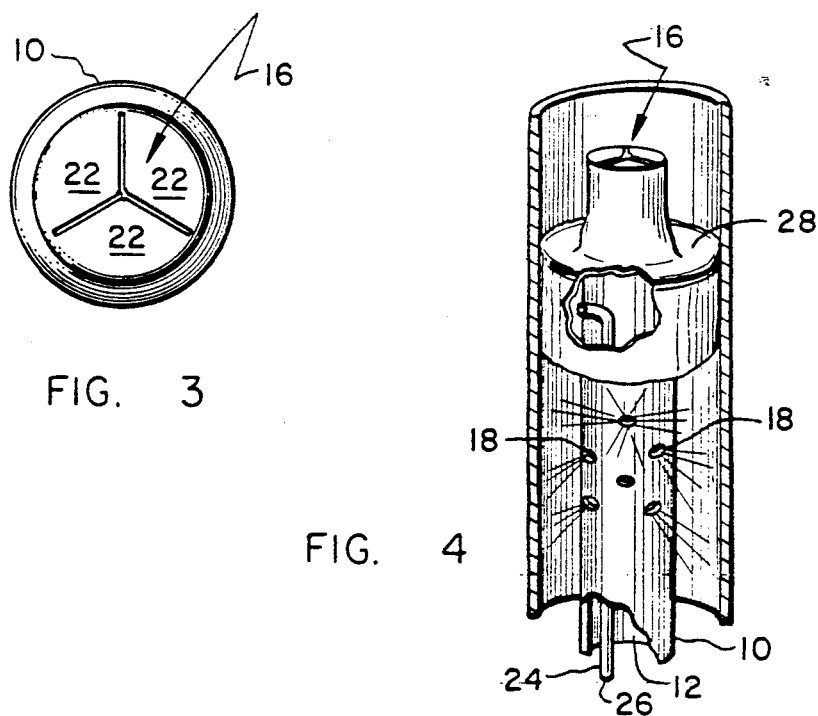
FIG. 3
FIG. 4

VALVED-TIP ANGIOGRAPHIC CATHETER

BACKGROUND OF THE INVENTION

Angiographic catheters are very small but long thin-walled tubes that are inserted into the human vascular system for diagnostic or therapeutic purposes. At the present time, almost all such catheters have an end-hole at the distal end so that the catheter can be passed over and guided by a wire which has been inserted into the vascular system through a hollow needle placed in a blood vessel. Also, because these catheters are open at both ends to allow passage over the guidewire, one catheter can be exchanged for another by replacing the wire and withdrawing the catheter over the wire.

When used in diagnostic procedures, the primary purpose of these catheters is to allow injection of radiopaque contrast material into the blood stream so as to produce an image of the blood vessel (an angiogram) on x-ray film. During the process of diagnostic angiography, the contrast medium is usually injected at a rapid rate using a power injector, and the contrast medium is forcefully discharged from the distal end-hole of the catheter creating a jet effect. This produces undesirable recoil of the catheter and can also produce a dangerous complication, subintimal injection of the contrast medium, in which the jet tunnels into the wall of the blood vessel sometimes resulting in acute occlusion of the vessel.

To minimize the undesirable effect of recoil and the potential complication of subintimal injection, some early catheter designs had sealed distal ends with side-holes near the distal end to allow injection of the contrast medium into the blood vessel laterally and symmetrically thereby reducing subintimal injections. Of course, with the sealed distal end, these catheters cannot be inserted into a blood vessel over a guidewire, and therefore this design is not widely used. Most catheters presently used for rapid flush angiography are configured with a circular loop or "pigtail" at the distal end. Although the end-hole is open, these pigtail type catheters are provided with side-holes through which approximately 40% of the contrast medium is discharged. Although the looped end of the catheter decreases somewhat the chance of subintimal injection, the open end-hole still allows approximately 60% of the contrast medium to exit the end-hole in a strong jet. During left ventriculography, this jet has been associated with the production of ventricular arrhythmias which can be dangerous to the patient and which can lessen the accuracy of the acquired physiologic data. To overcome the limitations of the pigtail catheter in cardiac angiography, various modifications have been attempted to the pigtail configuration, such as a multiple loop configuration or formation of a bend at an acute angle in the distal portion of the catheter. However, these modifications have not satisfactorily alleviated the problems associated with the use of any catheter which has an open end-hole.

Moreover, when catheters of this type are used during abdominal aortography, it is sometimes desirable to have the contrast medium injected in a lateral fashion to opacify the renal arteries which arise at right angles to the abdominal aorta. The pigtail catheter, including known modifications of it, tends to inject the contrast medium in a superior direction through the superiorly directed end-hole. This produces the undesirable effect of filling the blood vessels superior to the renal arteries which can obscure visualization of the anatomic structures being observed.

There is therefore a need for a catheter which can be inserted into the vascular system by passing it over a guidewire but which catheter will have the advantages of a closed-end catheter.

SUMMARY OF THE INVENTION

The catheter of the invention has formed over the end-hole at its distal end a two-way valve which opens to allow passage of a guidewire and closes upon removal of the guidewire to prevent discharge of fluid from the end-hole of the catheter. In one embodiment, the catheter is formed with side-holes for discharge of the fluid, such as a contrast medium, and the principles of the invention can be utilized in a balloon occlusion catheter because all of the fluid will be discharged proximally to the balloon through the end-holes. When used with a ballon for coronary or small vessel peripheral angioplasty, no side holes are formed in the catheter, thus creating a single lumen over-the-wire angioplasty ballon catheter. The valve at the distal end of the catheter may be formed by several slits along radial lines in a solid tubular piece of material similar to the material used in the catheter itself. However, the material must have sufficient elasticity so that the valve remains normally closed and is opened only when a guidewire is advanced in either direction against the valve.

BRIEF DESCRIPTION OF THE DRAWINGS

FIG. 1 is a perspective view of the distal end of a typical catheter of the intravascular type incorporating the principles of the invention;

FIG. 2 is a longitudinal cross-section of the catheter of FIG. 1 taken on the line 2—2 of FIG. 1;

FIG. 3 is an end view of a catheter constructed according to the invention and showing the valve at the distal end; and FIG. 4 is a perspective view that illustrates the principles of the invention as applied to a balloon occlusion catheter.

DESCRIPTION OF THE PREFERRED EMBODIMENTS OF THE INVENTION

The intravascular catheter of the invention has an elongated tubular wall 10 that defines a longitudinally extending lumen or passageway 12 extending throughout the length of the catheter. The catheter is constructed of any suitable material that has the required strength and flexibility which will permit the catheter to be inserted into a blood vessel for use in various diagnostic and therapeutic applications where it is necessary to inject a fluid, such as a contrast medium, into the body. There are a number of plastic materials presently available that are suitable for this use, such as various forms of soft polyurethanes, soft polyesters guidewire. When the guidewire is removed, the resiliency of the flaps 22 will once again close off the distal end 14.

The distal end 14 may be either normally straight as shown in the drawings, or distal end 14 may be shaped into a circular pigtail configuration similar to that of presently used catheters which have a closed distal end. The principles of the invention therefore can be applied to pigtail catheters which are used extensively in ventriculography.

In FIG. 4 there is illustrated a balloon occlusion catheter to which the principles of the invention have been applied by positioning valve 16 at the distal end. In this balloon occulsion catheter, there is in addition to the outer wall 10 an interior tube 24 that provides a passageway or lumen 26 which carries fluid, such as air, to an expandable wall or balloon 28 formed in the wall 10 near its distal end 14 downstream from the side-holes 18. The expandable wall or balloon 28 can therefore be inflated using lumen 26 so as to occlude flow through the blood vessel. As in the other embodiments of the invention, when the catheter is inserted into the blood vessel using a guidewire, as soon as the end of the guidewire engages the flaps 22 of valve 16, the flaps 22 will flex to permit passage of the guidewire until such time as it is withdrawn. When the guidewire is withdrawn, valve 16 will close and remain closed, thus allowing for all of the fluid flowing through passageway 12 to be discharged through side-holes 18.

The principles of the invention also can be applied to balloon catheters with no side holes, thereby allowing guidewire insertion and low density polyethylenes. The passageway 12 normally terminates in an end-hole or discharge opening at the distal end 14 of the catheter, but the invention provides a valve, indicated generally by the reference numeral 16, that covers the end-hole. Valve 16 may be formed in any suitable manner. For example, valve 16 may be formed at the outer end of a solid tubular end piece 20 of relatively short length which is fused or otherwise suitably attached at the distal end 14 of the wall 10 of the catheter.

The desired action of valve 16 may be created by a plurality of flaps 22 formed by one or more cuts, such as radially extending slits, in the outer end of end piece 20. In the alternative, a pin hole could be formed in the outer end of the end piece 20, the pin hole being just large enough to permit the passage of a guidewire. The flaps 22 are preferably formed of the same basic material as the material that forms the wall 10 of the catheter, but the material forming flaps 22 must have sufficient elasticity to perform the valve function in the manner described herein.

In one embodiment of the invention, upstream from the valve 16 are a plurality of side-holes 18 formed in the wall 10 of the catheter to provide for lateral discharge of fluid flowing through the passageway 12 of the catheter. The flaps 22 normally close the end-hole at distal end 14 and substantially seal off distal end 14 so that any fluid introduced into the passageway 12 is discharged through the side-holes 18. However, when the end of a guidewire (not shown) strikes the flaps 22 from either direction, the flaps 22 will bend a sufficient amount to permit the passage of the and balloon inflation through a single passageway. Similarly, the valved end construction utilizing the principles of the invention will allow an angioplasty balloon to be inflated through the same lumen used to pass the catheter over a guidewire thus creating a single lumen over-the-wire angioplasty balloon. This would allow the catheter diameter to be reduced significantly which would be useful in coronary angioplasty and small vessel peripheral angioplasty.

The operation and use of the catheter of the invention is evident from the foregoing description. When the catheter of the invention is properly used, catheter recoil will be greatly reduced if not eliminated since the contrast medium, for example, will be discharged from the catheter laterally in a symmetrical fashion through the side-holes. Also, use of the valved distal end will greatly reduce the chance of subintimal contrast injections since there will no longer be any jet effect from the end-hole. The catheter of the invention will also provide more accurate contrast injection in the aorta, since contrast medium is injected laterally through the side-holes. Also, infusion of other fluids, such as thrombolytic agents, is improved since these fluids can be infused evenly through multiple side-holes rather than a single end-hole of the catheter. Moreover, the catheter of the invention may be useful in nonvascular catheter applications, such as in biliary and renal catheterization procedures.

It will be thus evident to those skilled in the art that there are numerous applications for the principles of the invention and that various revisions and modifications can be made to the preferred embodiments disclosed herein without departing from the spirit and scope of the invention. It is my intention, however, that all such revisions and modifications as are obvious to those skilled in the art will be included within the scope of the following claims.

What is claimed is:

1. A catheter insertable over a guidewire for introducing a fluid into a vessel of the human body, said catheter comprising a long hollow flexible tube of the desired length having a small diameter and a proximal end and a distal end, said tube having a thin wall extending between said ends to define a passageway extending throughout the length of the tube and terminating at the distal end, a plurality of side holes extending through the wall of the tube near its distal end to provide for the discharge of fluid from the passageway through the holes in the wall and into the vessel, and means closing the distal end and preventing the discharge of fluid from the passageway through the distal end, said means opening during the passage of the guidewire through the distal end.

2. The catheter of claim 1 in which the means closing the distal end is comprised of a plurality of resilient flaps that normally close off the distal end but which will flex to allow the passage of the guidewire.

3. The catheter of claim 2 in which the flaps are formed by a plurality of radial slits.

4. The catheter of claim 1 in which there is an opening in the means closing the distal end which opening is small enough to allow the passage of the guidewire without allowing the passage of fluid from the distal end.

5. A catheter for introducing a fluid into the body, said catheter comprising a tube of the desired length having a proximal end and a distal end, a thin wall extending between said ends to define a passageway extending throughout the length of the tube, the distal end terminating in an end hole that is in communication with the passageway, a plurality of side holes extending through the wall of the tube near its distal end to provide for the flow of fluid from the passageway through the wall, an inflatable means near the distal end between the side holes and the end hole, said inflatable means being normally not inflated, pressure means to controllably inflate the inflatable means from the proximal end, and valve means comprised of a plurality of resilient flaps formed by a plurality of radial slits that normally close off the end hole to prevent the discharge of fluid from the passageway through the end hole but which will flex to allow the passage of a guidewire through the valve means.

6. The catheter of claim 5 in which the pressure means includes a tube positioned inside of the passageway and extending from the proximal end terminating at the inflatable means.

* * * * *